United States Patent [19]

Koyama et al.

[11] 4,333,870
[45] Jun. 8, 1982

[54] PROCESS FOR SEPARATING γ-GLOBULIN AGGREGATE BY POLYSULFONE MEMBRANE

[75] Inventors: Kenji Koyama; Syotaro Ohno, both of Tokuyama; Mitsutoshi Fukuda, Shin-nanyo, all of Japan

[73] Assignee: Toyo Soda Manufacturing Co., Ltd., Yamaguchi, Japan

[21] Appl. No.: 188,118

[22] Filed: Sep. 17, 1980

[30] Foreign Application Priority Data

Oct. 22, 1979 [JP]  Japan .................................. 54-135137

[51] Int. Cl.³ .............................................. C07G 7/00
[52] U.S. Cl. .................................. 260/112 B; 424/101
[58] Field of Search ...................... 260/112 B; 424/101

[56] References Cited

U.S. PATENT DOCUMENTS

| | | | |
|---|---|---|---|
| 3,664,994 | 5/1972 | Perper | 260/112 B |
| 3,808,189 | 4/1974 | Brever | 260/112 B |
| 3,928,580 | 12/1975 | Fontaine | 260/112 B |
| 4,163,010 | 7/1979 | Garbutt | 260/112 R |

FOREIGN PATENT DOCUMENTS 1011013 11/1965 United Kingdom .

OTHER PUBLICATIONS

Condensed Chemical Dictionary 8th Ed., p. 712, 1971.
Introduction to Polymer Sci. and Technology, pp. 47–49, 1970.
Chem. Abstracts, vol. 76, 1972, 155127q, Bourat et al.

*Primary Examiner*—Howard E. Schain
*Attorney, Agent, or Firm*—Oblon, Fisher, Spivak, McClelland & Maier

[57] ABSTRACT

γ-Globulin aggregate is separated by a membrane from an aqueous solution of γ-globulin through an ultrafiltration membrane. The ultrafiltration membrane is a membrane made of a polysulfone resin having the formula

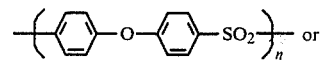

or

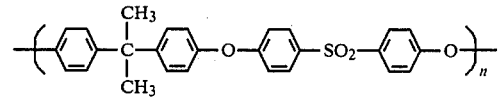

(n = 50 to 250)

3 Claims, 5 Drawing Figures

PROCESS FOR SEPARATING γ-GLOBULIN AGGREGATE BY POLYSULFONE MEMBRANE

BACKGROUND OF THE INVENTION

1. Field of the Invention

The present invention relates to a process for separating γ-globulin aggregate for preparing γ-globulin medicine which does not contains γ-globulin aggregate. More particularly, it relates to a process for separating γ-globulin aggregate by an ultrafiltration membrane to obtain a γ-globulin medicine which is not chemically modified so as to be suitable for intravenous administration.

2. Description of the Prior Art

Among immunoglobulin as a component of plasma proteins, γ-globulin medicine comprising IgG as a main component has been used for prevention and therapeutic of various infection diseases, however, the medicine causes severe anaphylactic reaction due to γ-globulin aggregate, and accordingly, it has been limited to intramuscular injection. In view of medical importance of the medicine, it has been proposed to administrate it by the intravenous administration so as to be further effective administration at large dose in immediate effect.

In order to be capable of the intravenous administration of γ-globulin medicine, it is necessary to reduce an anticomplementary activity as a result of the side-effect. It has been confirmed that the anticomplementary activity is resulted by the aggregation of γ-globulin in the separation of γ-globulin monomer. Certain processes for separating the γ-globulin aggregate or reducing the anticomplementary activity are as follows:

(1) Enzymic treatment
  [Vox Sang. 13 71 (1967)]
(2) Chemical modification
  [Vox Sang. 28 422 (1965)]
  [Japanese Unexamined Patent Publication 103723/1973]
(3) Process for deaggregating the aggregate in γ-globulin medicine
  [Acta Chemica Scandinavia 22 490 (1968)]

The process (1) for treating immunoglobulin with pepsin to remove the complement-fixing site has disadvantages that the half-life of antibody activity of γ-globulin in blood is remarkably short and the Fc activity can not be expected.

The process (2) has the disadvantage which is different from the natural condition as intact γ-globulin monomer.

The process (3) is the optimum process for obtaining intact γ-globulin monomer. The product, however result in the aggregate in storage to increase the anticomplementary activity.

SUMMARY OF THE INVENTION

It is an object of the present invention to overcome these disadvantages from different viewpoints and to obtain intact γ-globulin monomer as the ideal medicine.

The foregoing and other objects of the present invention is to provide a process for separating γ-globulin monomer in relatively simple and speedy by selectively separating it in the condition for permeating γ-globulin monomer through a membrane without permeating γ-globulin aggregate by an ultrafiltration membrane.

DETAILED DESCRIPTION OF THE PREFERRED EMBODIMENTS

Figure 1:
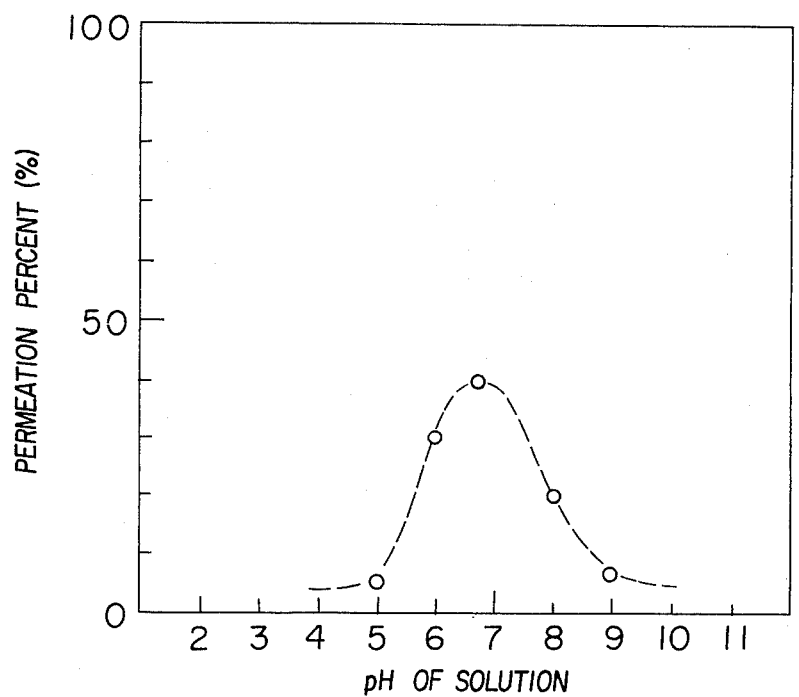
FIG. 1 shows the relation of pH of the solutions in examples and permeation percent of γ-globulin monomer.

The pore diameter of the membrane can not be observed by an electron microscope. In the case of the ultrafiltration membrane, it is usual to define the property of a membrane by a cut-off molecular weight.

A cut-off molecular weight is usually defined by measuring retention percents of the membrane with a spherical protein having the known molecular weight (1-concentration of permeated solution/concentration of original solution)×100 and plotting the molecular weights of the solute and the retention percents and calculating the molecular weight at the retention percent of 100%. The cut-off molecular weight may be varied depending upon the process of measurement. For example, PM-10 membrane manufactured by Amicon Co. is referred as a fraction molecular weight of 10,000, however, myoglobin having a molecular weight of 18,000 is permeated through the membrane.

The cut-off molecular weight of the ultrafiltration membrane used in the present invention is usually in a range of $2\times10^5$ to $3.5\times10^5$ preferably $2.5\times10^5$ to $3\times10^5$. The cut-off molecular weight is varied depending upon the process for measurement. For example, the cut-off molecular weight is varied depending upon the variation of pH of the solution even though the sample and the membrane are the same. The variation is considered depending upon charges of the protein and distribution of the protein in the solution.

In this case, the cut-off molecular weight is determined by using proteins having known molecular weights in a phosphate buffer solution (pH: 6.8) as an elute of an aqueous gel permeation chromatography (GPC), measuring ratios of absobauces of the sample at 280 mm by G3000SW column manufactured by Toyo Soda Mfg. Co. and plotting the retention percents of the membrane. The proteins used for the measurement include myoglobin, γ-lactoglobulin, albumin, γ-globulin and glutamate dehydrogenase. In the present invention, the cut-off molecular weight at pH of 6.8 is given. The process for measuring the retention percent is not limited to the process of the present invention.

Among ultrafiltration membranes having the same cut-off molecular weight, membranes made of a polyamide, a polyethyleneterephthalate, a polycarbonate, cellulose or cellulose acetate sometimes permeate aggregates as well as monomers and have inferior separatability. For example, when a cellulose membrane is used, γ-globulin adsorbed on the membrane to be remarkably lower ultrafiltration rate. On the contrary, when a polysulfone resin membrane is used, an ultrafiltration membrane having remarkably narrow distribution of pore diameters can be obtained to give a constant ultrafiltration rate without any adsorption of γ-globulin on the membrane. This is the optimum membrane for separating γ-globulin monomer. Therefore, it has been possible to separate the components depending upon difference of sizes as the feature of ultrafiltration membrane. Thus, the membrane separation of γ-globulin monomer from the aqueous solution containing γ-globulin aggregate has been attained by a simple and speedy process depending upon difference of sizes of the γ-globulin monomer and γ-globulin aggregate.

The polysulfone resins have the following unit structure.

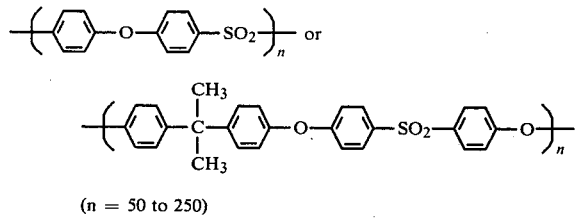

(n = 50 to 250)

The membrane can be prepared by dissolving the polysulfone in a solvent and then, the solution is spread in a form of a film and is immersed into a non-solvent.

In the separation with the membrane, pH of the aqueous solution is preferably in a range of 6 to 8 especially 6.5 to 7.5. The permeation percent of γ-globulin monomer (concentration of permeated solution/concentration of original solution×100) is remarkably varied depending upon pH. The time for membrane separation is shorter as a membrane of higher permeation percent of γ-globulin monomer is used. In view of the economical problem, the optimum pH in the separation with the membrane is preferably in a range of 6 to 8 especially 6.5 to 7.5. The concentration of the solution is usually lower than 5% (W/V) preferably lower than 2% (W/V). When it is higher, the ultrafiltration rate is lower and the permeation percent of γ-globulin monomer is lower, because a concentration polarization of the solute on the surface of the membrane is higher.

In accordance with the process of the present invention, the pH of the aqueous solution containing γ-globulin aggregate is adjusted in a range of 6 to 8. The ultrafiltration of the solution through the membrane was carried out to remain γ-globulin aggregate on the membrane and to permeate γ-globulin monomer through the membrane. Then, the γ-globulin monomer solution permeated is concentrated with a membrane having cut-off molecular weight below $10^5$.

The process of the present invention can be applied not only for the γ-globulin solution containing γ-globulin aggregate derived from human γ-globulin but also for the solutions containing γ-globulin aggregate derived from animals such as cattle, horse and sheep.

The present invention will be illustrated by certain examples and references which are provided for purposes of illustration only and are not intended to be limiting the present invention.

EXAMPLE 1

Polysulfone resin P-1700 manufactured by UCC was dissolved in N-methyl-2-pyrrolidone to prepare 15% solution. The solution was spread on polyethylene nonwoven fabric having a size of 30 cm×30 cm to be a thickness of 100μ by a doctor-knife and was dipped into water to obtain a membrane.

Figure 2:
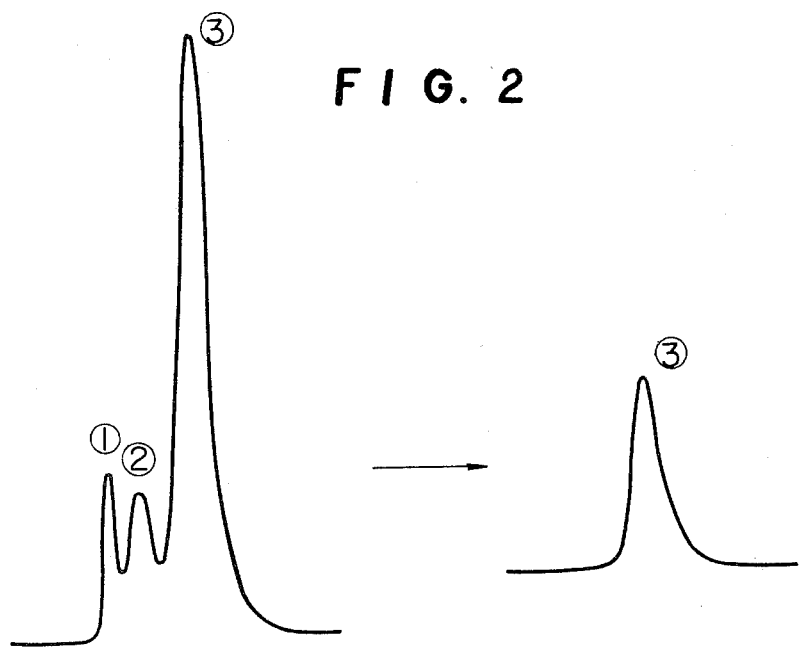
FIGS. 2, 3 and 5 show the liquid chromatogram as the results of the example of the present invention.

The cut-off molecular weight of the membrane was measured by cutting the membrane in a size of a diameter of 43 mm and equipping it with a ultrafiltration apparatus to measure retention percents of proteins of myoglobin (18,000), albumin (68,000), γ-globulin (160,000) and glutamate dehydrogenase (360,000). The cut-off molecular weight is about $3\times10^5$. An aqueous solution of γ-globulin containing γ-globulin aggregate derived from human-body was dissolved into a phosphate buffer solution having pH of 6.8 to prepare 1% solution. The solution was treated in the membrane separation by an ultrafiltration apparatus equipped with the membrane. The results are shown in FIG. 2.

It is clear that only γ-globulin monomer is permeated through the membrane by the chromatography. The permeation percent of γ-globulin monomer was about 40%. The chromatogram was measured by the apparatus used for the measurement of the cut-off molecular weight. In FIG. 2, the reference ① designates the polymer; ② designates the dimer and ③ designates the monomer. The left side shows the chromatogram of the original solution and the right side shows the chromatogram of the permeated solution.

EXAMPLE 2

Figure 3:
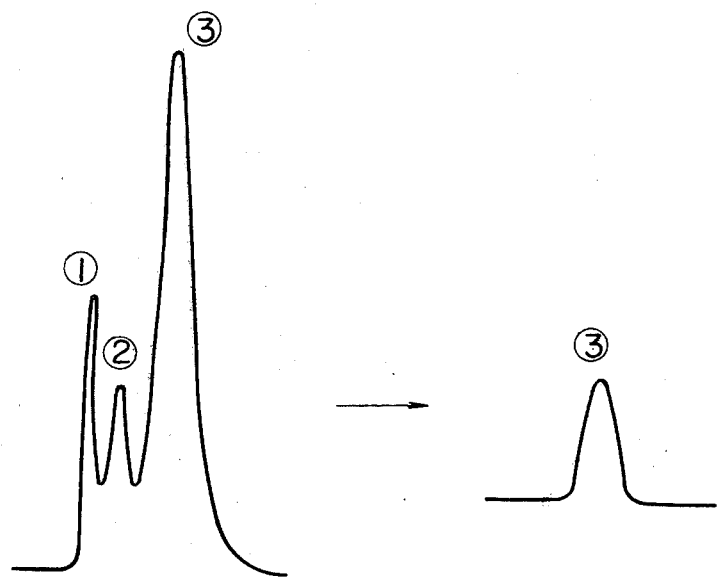

In accordance with the process of Example 1, a membrane separation of an aqueous solution of bovine serum γ-globulin in pH of 7.5 was carried out. The results are shown in FIG. 3. Only γ-globulin monomer was permeated through the membrane. The permeation percent of γ-globulin monomer was about 30%.

REFERENCE 1

Figure 4:
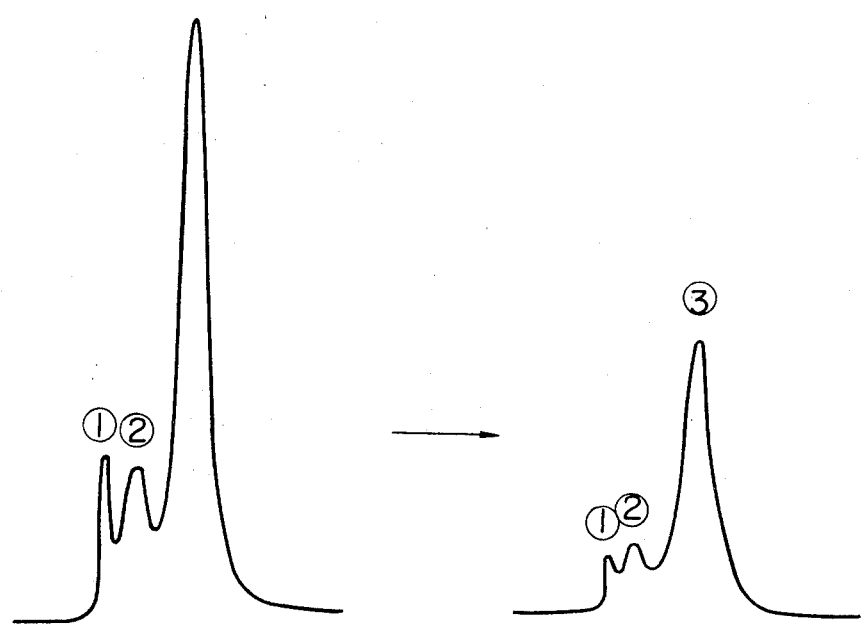
FIG. 4 shows the liquid chromatogram as references in different conditions.

In accordance with the process of Example 1, polysulfone resin P-1700 manufactured by UCC was dissolved into N-methyl-2-pyrrolidone to prepare 10% solution and a membrane was prepared and the cut-off molecular weight was measured. As the result, the cut-off molecular weight of the membrane was about $5\times10^5$. γ-Globulin aggregate derived from human-body was dissolved in a phosphate buffer solution having pH of 6.8 to prepare 1% solution. In accordance with the process of Example 1, a membrane separation of the solution was carried out. The results are shown in FIG. 4. According to the chromatogram, it was found that a relatively large amount of γ-globulin aggregate was permeated.

REFERENCE 2

In accordance with the process of Example 1, a membrane separation of the solution in pH of 4 was carried out. As a result, the permeation percent of γ-globulin monomer was remarkably low as about 5%.

EXAMPLE 3

Polysulfone resin having the formula

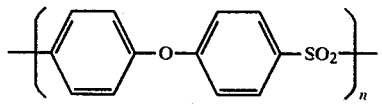

Figure 5:
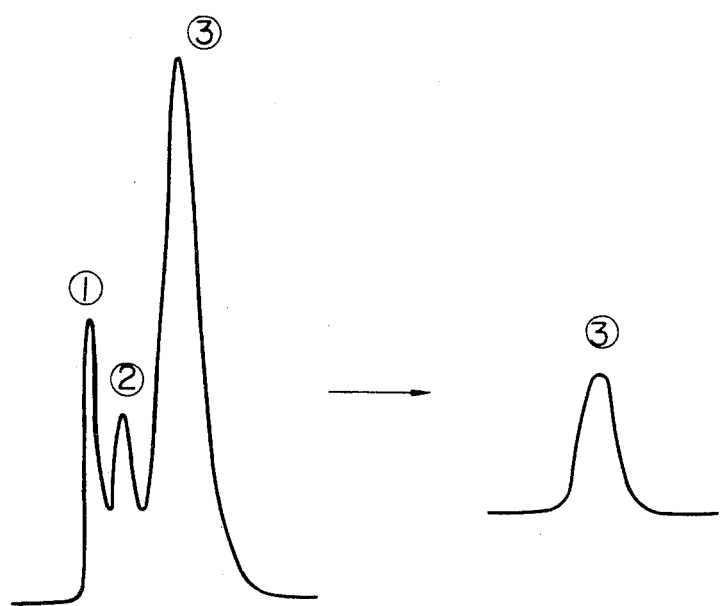

(n = 200)

was dissolved into N-methyl-2-pyrrolidone to prepare 15% solution. In accordance with the process of Example 1, a membrane was prepared and a cut-off molecular weight of the membrane was measured to be about $2.5\times10^5$. In accordance with the process of Example 2, a membrane separation of an aqueous solution of bovine serum γ-globulin in pH of 7.0 was carried out. The results are shown in FIG. 5. It is clear that only γ-globulin monomer permeated through the membrane. The permeation percent of γ-globulin monomer was about 30%.

We claim:

1. A process for separating γ-globulin aggregate by a membrane which comprises separating γ-globulin aggregate from an aqueous solution of γ-globulin through an ultrafiltration membrane made of a polysulfone resin having the formula

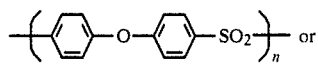

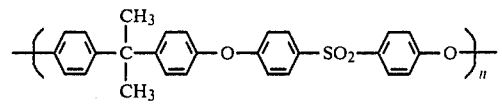

(n = 50 to 250)

2. The process according to claim 1 wherein pH of said aqueous solution is in a range of 6 to 8.
3. The process according to claim 1 wherein the cutoff molecular weight of the ultrafiltration membrane is in range of $2 \times 10^5$ to $3.5 \times 10^5$.